United States Patent
Powers

(10) Patent No.: US 8,331,574 B2
(45) Date of Patent: Dec. 11, 2012

(54) AUTOMATIC EXTERNAL DEFIBRILLATOR WITH ENHANCED CLARITY OF AUDIBLE PROMPTS

(75) Inventor: Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 877 days.

(21) Appl. No.: 12/299,482

(22) PCT Filed: May 3, 2007

(86) PCT No.: PCT/IB2007/051670
§ 371 (c)(1),
(2), (4) Date: Nov. 4, 2008

(87) PCT Pub. No.: WO2007/129267
PCT Pub. Date: Nov. 15, 2007

(65) Prior Publication Data
US 2009/0092260 A1    Apr. 9, 2009

Related U.S. Application Data

(60) Provisional application No. 60/746,960, filed on May 10, 2006.

(51) Int. Cl.
*H04R 29/00*    (2006.01)
(52) U.S. Cl. ............... 381/56; 381/57; 381/58; 381/67; 381/94.1; 607/5; 607/32
(58) Field of Classification Search .................... 381/57, 381/56, 58, 94.1, 67; 607/5, 32
See application file for complete search history.

(56) References Cited

U.S. PATENT DOCUMENTS

| | | | |
|---|---|---|---|
| 4,061,874 A | 12/1977 | Fricke et al. | |
| 5,434,922 A | 7/1995 | Miller et al. | |
| 5,792,204 A * | 8/1998 | Snell | 607/32 |
| 5,907,823 A | 5/1999 | Sjoberg et al. | |
| 6,021,349 A * | 2/2000 | Arand et al. | 607/5 |
| 2003/0032988 A1 | 2/2003 | Fincke | |
| 2003/0059034 A1 | 3/2003 | Etter | |
| 2005/0063552 A1 | 3/2005 | Shuttleworth et al. | |

FOREIGN PATENT DOCUMENTS

| | | |
|---|---|---|
| WO | 2005074129 A | 8/2005 |
| WO | 2005016288 A | 2/2006 |
| WO | 2006102425 A | 9/2006 |

* cited by examiner

*Primary Examiner* — Tan N Tran
(74) *Attorney, Agent, or Firm* — W. Brinton Yorks, Jr.

(57) ABSTRACT

An automatic external defibrillator produces audible prompts for a user by providing the audible information with default audio characteristics in response to a first ambient noise condition and providing the audible information having different audio characteristics than the default audio characteristics in response to a second ambient noise condition. An automatic external defibrillator provides voice prompts by selecting one of a plurality of different levels of sound quality at which to playback the voice prompts and playing back the voice prompts at the selected level of sound quality.

7 Claims, 6 Drawing Sheets

AUTOMATIC EXTERNAL DEFIBRILLATOR WITH ENHANCED CLARITY OF AUDIBLE PROMPTS

The invention relates generally to electrotherapy circuits, and more particularly, to automatic external defibrillators which include a system and method for enhancing the clarity of audible prompts in acoustically challenging environments.

Automatic external defibrillators ("AEDs") deliver a high-voltage impulse to the heart in order to restore normal rhythm and contractile function in patients who are experiencing arrhythmia, such as ventricular fibrillation ("VF") or ventricular tachycardia ("VT") that is not accompanied by a palpable pulse. There are several classes of defibrillators, including manual defibrillators, implantable defibrillators, and automatic external defibrillators. AEDs differ from manual defibrillators in that AEDs they are pre-programmed to automatically analyze an electrocardiogram ("ECG") rhythm to determine if defibrillation is necessary and to provide administration measures such as shock sequences and cardio-pulmonary resuscitation ("CPR") periods.

FIG. 1 is an illustration of an AED 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be app lied after the onset of VF, the better the chances that the patient 14 will survive the cardiac event.

In the use of the AED a pair of electrodes 16 are applied across the chest of the patient 14 by the user 12 in order to acquire an ECG signal from the patient's heart. The defibrillator 10 then analyzes the ECG signal for signs of arrhythmia. If a treatable arrhythmia is detected, the defibrillator 10 signals the user 12 that a shock is advised. After detecting VF or other shockable rhythm, the user 12 then presses a shock button on the defibrillator 10 to deliver defibrillation pulses to resuscitate the patient 14.

Many AEDs use audible prompts to instruct an untrained user to correctly deliver shock therapy to a patient. The prerecorded audible prompts are played back by an audio system included in the AED so that the proper protocol for administering therapy can be followed, as well as provide audible warnings to stand clear of the patient when a shock is delivered. Since untrained users may be provided with little guidance in operating the AED except for the audible prompts, it is important during emergency situations that the audible prompts be clearly understood. The ambient noise in the environment in which the AED is being used can vary greatly, for example, from a relatively quiet and controlled situation to a loud environment, such as a roadside, an airplane, or an open space surrounded by bystanders. In these environments, good sound quality is secondary to the paramount importance of enabling the rescuer to clearly hear and understand the audible prompts.

One approach to increasing audibility is to increase the playback volume of the audible prompts. This is a straightforward approach, but its effectiveness is limited by the capabilities of the audio system included in the AED to reproduce the audible prompts at a sufficient volume and with limited distortion so that the audible prompts can be heard over ambient noise and do not become unintelligible. The sound quality of the audible prompts can also affect the overall audibility of the prompts. Higher-quality audible prompts, that is, audible prompts having good bandwidth and dynamic range, may be desirable in some applications, such as when the AED is being used for training or demonstration purposes. The environments during this type of use are typically more controlled and will have less background noise to conflict with the audible prompts. However, the higher-quality audio of the audible prompts should be readily traded off when noisy rescue situations call for clarity in understanding the audible prompts as a higher priority. The prerecorded audible prompts that are played back by the AED should not be a compromise between sound quality and audibility that do not fully satisfy the requirements of either a calm environment or a noisy one.

Therefore, there is a need for an AED providing enhanced clarity of audible prompts when used in noisy environments while maintaining the quality of the audible prompts when the AED is used in less acoustically challenging environments.

In accordance with the one aspect of the present invention an AED provides audible information by providing the audible information having default audible characteristics in response to a first ambient noise condition and providing the audible information having different audible characteristics than the default audible characteristics in response to a second ambient noise condition.

In accordance with another aspect of the present invention an AED provides voice prompts by selecting or enabling user selection of one of a plurality of different levels of sound quality at which to play back the voice prompts and playing back the voice prompts at the selected level of sound quality.

In accordance with another aspect of the present invention an AED includes an audio system operable to provide audible information and further includes a controller coupled to the audio system and operable to control the audio system to provide the audible information and further operable to select one of a plurality of different levels of sound quality at which the audio system provides the audible information.

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, and software operations have not been shown in detail in order to avoid unnecessarily obscuring the invention.

Figure 1:
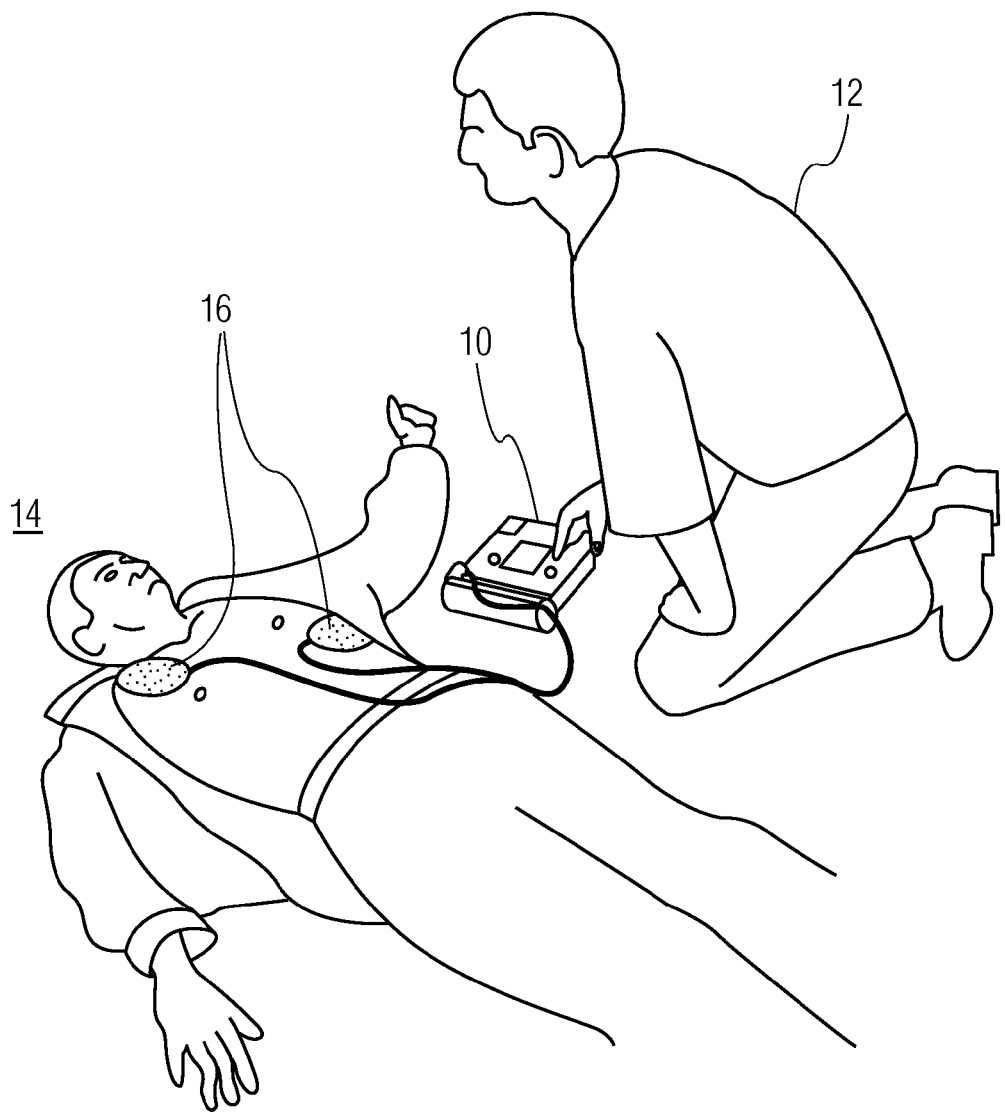
FIG. 1 is an illustration of a defibrillator being applied to a patient suffering from cardiac arrest.
Figure 2:
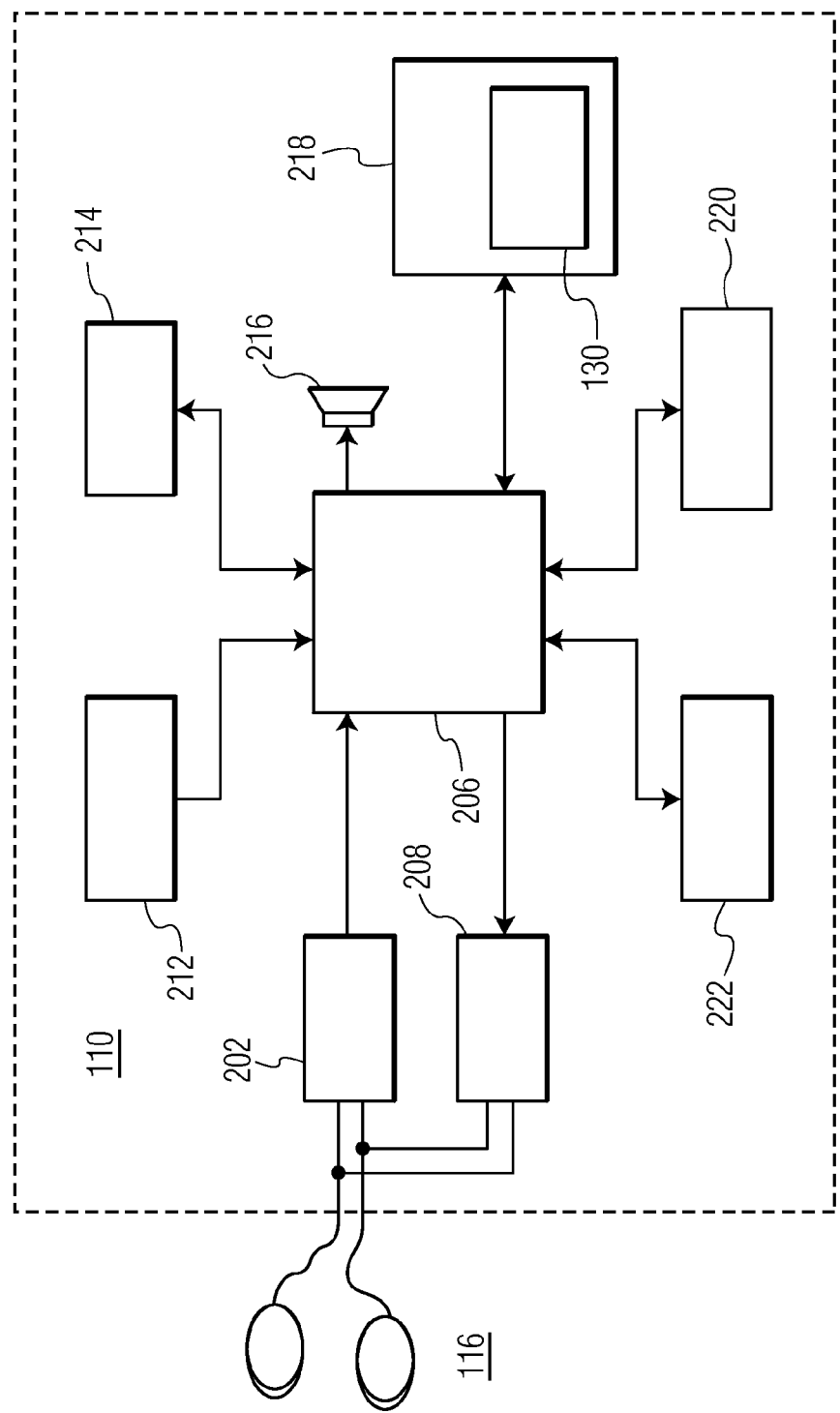
FIG. 2 is a block diagram of a defibrillator constructed in accordance with the principles of the present invention.

FIG. 2 illustrates an AED 110 constructed in accordance with the principles of the present invention. The AED 110 is designed for small physical size, light weight, and relatively simple user interface capable of being operated by personnel without high training levels or who otherwise would use the defibrillator 110 only infrequently. In contrast, a paramedic or clinical (manual) defibrillator of the type generally carried by an emergency medical service ("EMS") responder tends to be larger, heavier, and have a more complex user interface capable of supporting a larger number of manual monitoring and analysis functions and protocol settings.

An ECG front end circuit 202 is connected to a pair of electrodes 116 that are connected across the chest of the patient 14. The ECG front end circuit 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV (high voltage) delivery circuit 208 to charge a high voltage capacitor of circuit 208 in preparation for delivering a shock, and a shock button on a user interface 214 is activated to begin flashing. The user interface 214 may consist of a display and control buttons such as an on-off button and a shock button for providing user control as well as visual information. A user interface of the present invention may also include one or more control buttons for selecting a rescue protocol stored in memory 218 to be carried out during a rescue. An audio speaker 216 delivers audible prompts to the user. The user 12 is then advised by an audible instruction to keep away from the patient ("hands off" instruction). When the user presses the shock button on the user interface 214 a defibrillation shock is delivered from the HV delivery circuit 208 to the patient 14 through the electrodes 116.

The controller 206 is coupled to further receive input from a microphone 212. The microphone 212 can be used to produce a voice strip, with the analog audio signal from the microphone 212 preferably being digitized to produce a stream of digitized audio samples which may be stored as part of an event summary 130 in a memory 218. In accordance with the present invention, the microphone 212 can also be used for measuring the ambient noise of the surrounding environment of the AED 110 during use. The memory 218, implemented either as on-board RAM, a removable memory card, or a combination of different memory technologies, operates to store the event summary 130 digitally as it is compiled during the treatment of the patient 14. The event summary 130 may include the streams of digitized ECG, audio samples, and other event data as previously described.

The memory 218 further operates to store data files, such as encoded audio data files for audible prompts played back through the audio speaker 216. The audio files are retrieved from the memory 218 and an audio processor 220 coupled to the controller 206 decodes the audio files for playback by the audio speaker. Conventional audio data formats such as MP3, WMA, and AAC, or audio data formats later developed, can be used for the audio files and audio processor 220. As will be described in more detail below, a digital signal processor ("DSP") 222 coupled to controller 206 can be included in the AED 110 for signal processing the decoded audio data before playback by the audio speaker 216. The signal processing performed by the DSP 222 can enhance the quality of the audible prompts when played back. The audio speaker 216, audio processor 220, and optional DSP 222 are an example of an audio system included in the AED 110. Although the audio processor 220 and the DSP 222 are shown as separate components in FIG. 2, they may be implemented by a combination of software and hardware or merely software where sufficient processing capabilities are available in the AED 110.

The AED 110 of FIG. 2 has several modes of operation that may be selected during operation of the AED 110. One mode of operation is a demonstration mode where various features can be demonstrated without the need for actual operation of the AED 110. Another mode of operation is an administration mode in which the AED 110 can be set up according to the user's preferences, reprogrammed for software upgrades, and the various modes of operation can be selected. A training mode of operation can be included as well. While in the training mode, a user is guided through operation of the AED 110 in a simulated emergency situation without the hazard of actually delivering shock therapy. In an actual emergency where the AED 110 is being used to provide shock therapy, the AED 110 operates in an emergency mode where operation is as previously described. The AED 110 is typically set in the emergency mode of operation upon power-up. However, the mode of operation can be changed using the controls of the user interface 214.

Figure 3:
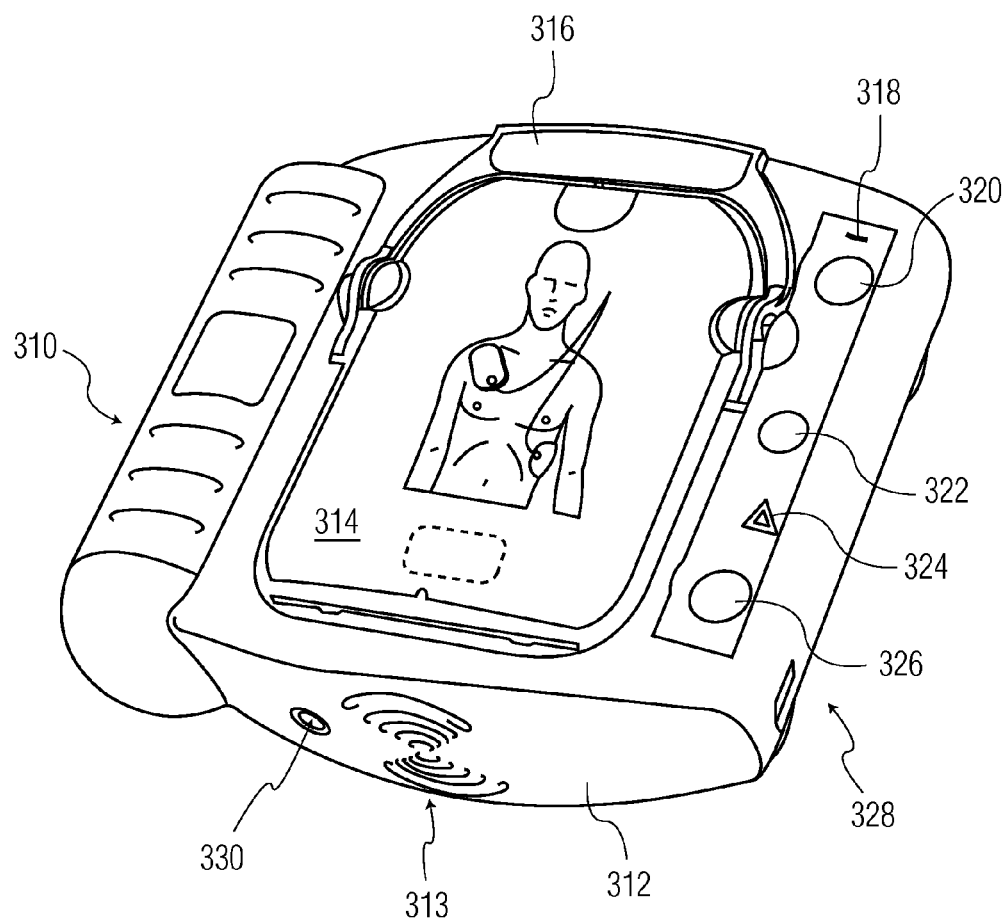
FIG. 3 illustrates an AED with an audible user interface.

Referring now to FIG. 3, an over-the-counter (OTC) AED 310 is shown in a top perspective view. The internal circuitry and operation of the OTC AED 310 is similar to that previously described and illustrated in FIG. 2. Those ordinarily skilled in the art will obtain sufficient understanding from the description provided herein to make any necessary modifications for implementing the OTC AED 310. The OTC AED 310 is housed in a rugged polymeric case 312 which protects the electronic circuitry inside the case and also protects the layperson user from shocks. Attached to the case 312 by electrical leads are a pair of electrode pads. In the embodiment of FIG. 3 the electrode pads are in a cartridge 314 located in a recess on the top side of the OTC AED 310. The electrode pads are accessed for use by pulling up on a handle 316 which allows removal of a plastic cover over the electrode pads. The user interface is on the right side of the AED 310. A small ready light 318 informs the user of the readiness of the OTC AED. In this embodiment the ready light blinks after the OTC AED has been properly set up and is ready for use. The ready light is on constantly when the OTC AED is in use, and the ready light is off or flashes in an alerting color when the OTC AED needs attention.

Below the ready light is an on/off button 320. The on/off button is pressed to turn on the OTC AED for use. To turn off the OTC AED a user holds the on/off button down for one second or more. An information button 322 flashes when information is available for the user. The user depresses the information button to access the available information. A caution light 324 blinks when the OTC AED is acquiring heartbeat information from the patient 14 and lights continuously when a shock is advised, alerting the user 12 and others that no one should be touching the patient 14 during these times. Interaction with the patient 14 while the heart signal is being acquired can introduce unwanted artifacts into the detected ECG signal and should be avoided. A shock button 326 is depressed to deliver a shock after the OTC AED informs the user 12 that a shock is advised. An infrared port 328 on the side of the OTC AED is used to transfer data between the OTC AED and a computer. This data port is used for communication after a patient 14 has been rescued and a physician desires to have the OTC AED event data downloaded to his or her computer for detailed analysis. A speaker 313 provides voice instructions to a user 12 to guide the user through the use of the OTC AED to treat a patient 14. A beeper 330 is provided which "chirps" when the OTC AED needs attention such as electrode pad replacement or a new battery.

Figure 4:
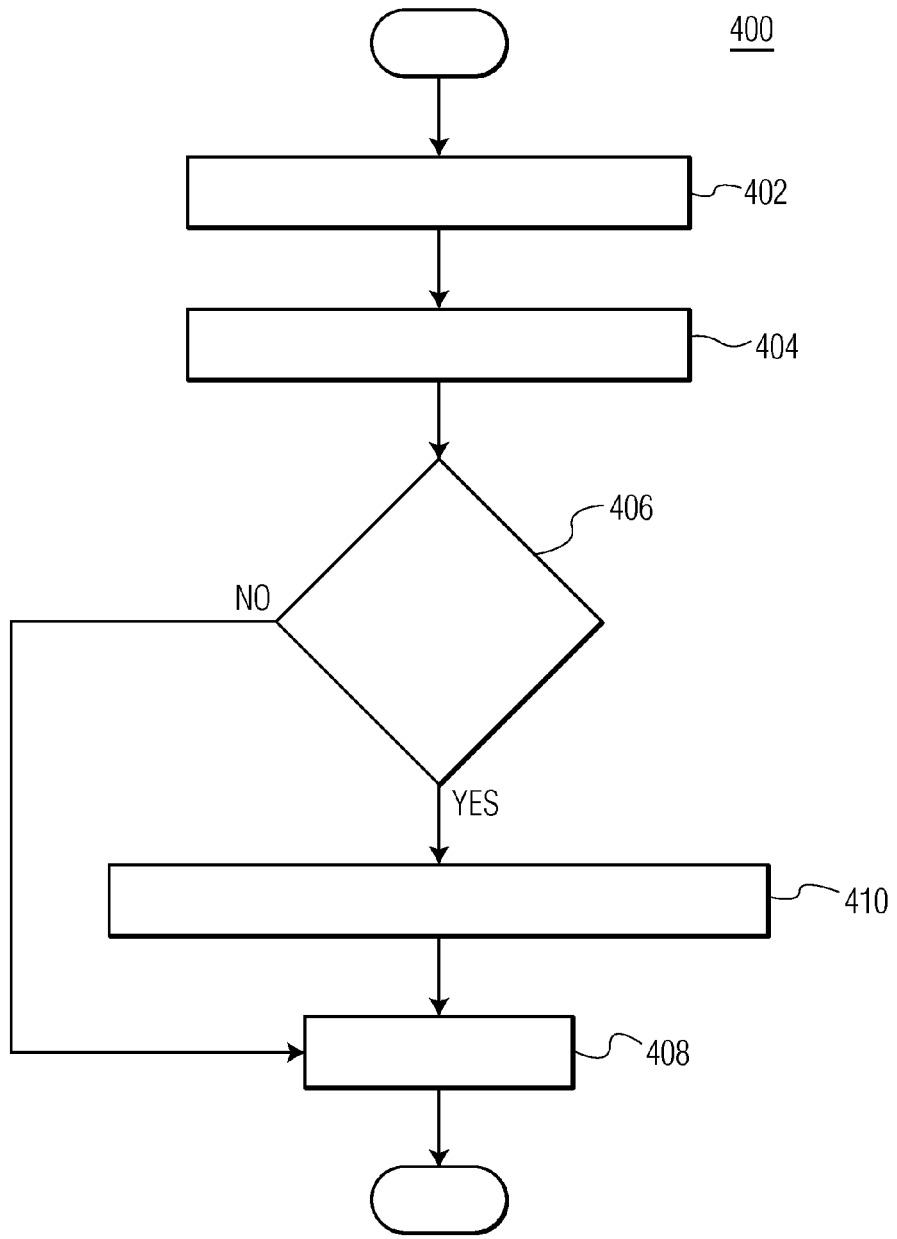
FIG. 4 is a flow diagram for enhancing the audibility of audible prompts according to an embodiment of the present invention that can be utilized in an AED.
Figure 5:
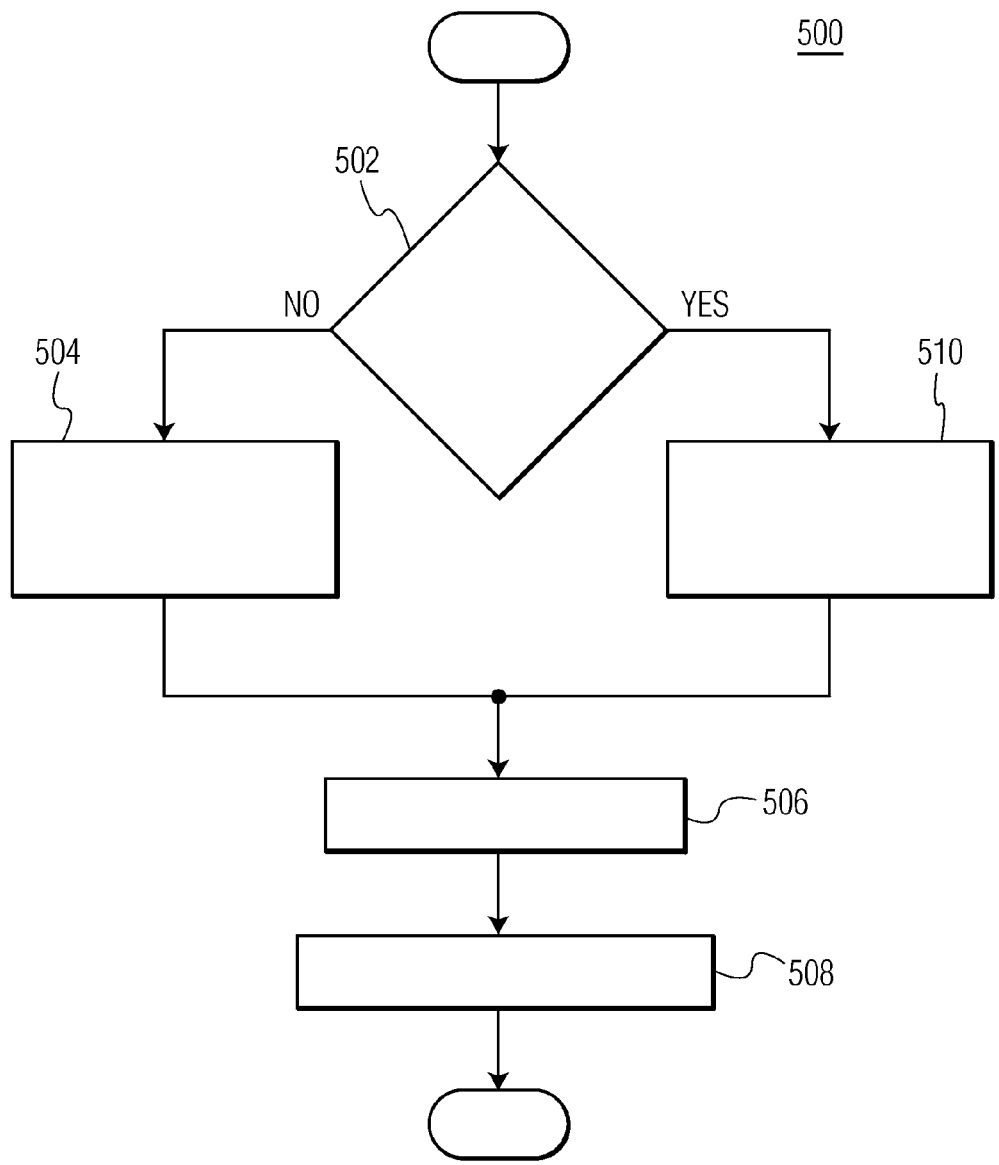
FIG. 5 is a flow diagram for enhancing the audibility of audible prompts according to another embodiment of the present invention that can be utilized in an AED.
Figure 6:
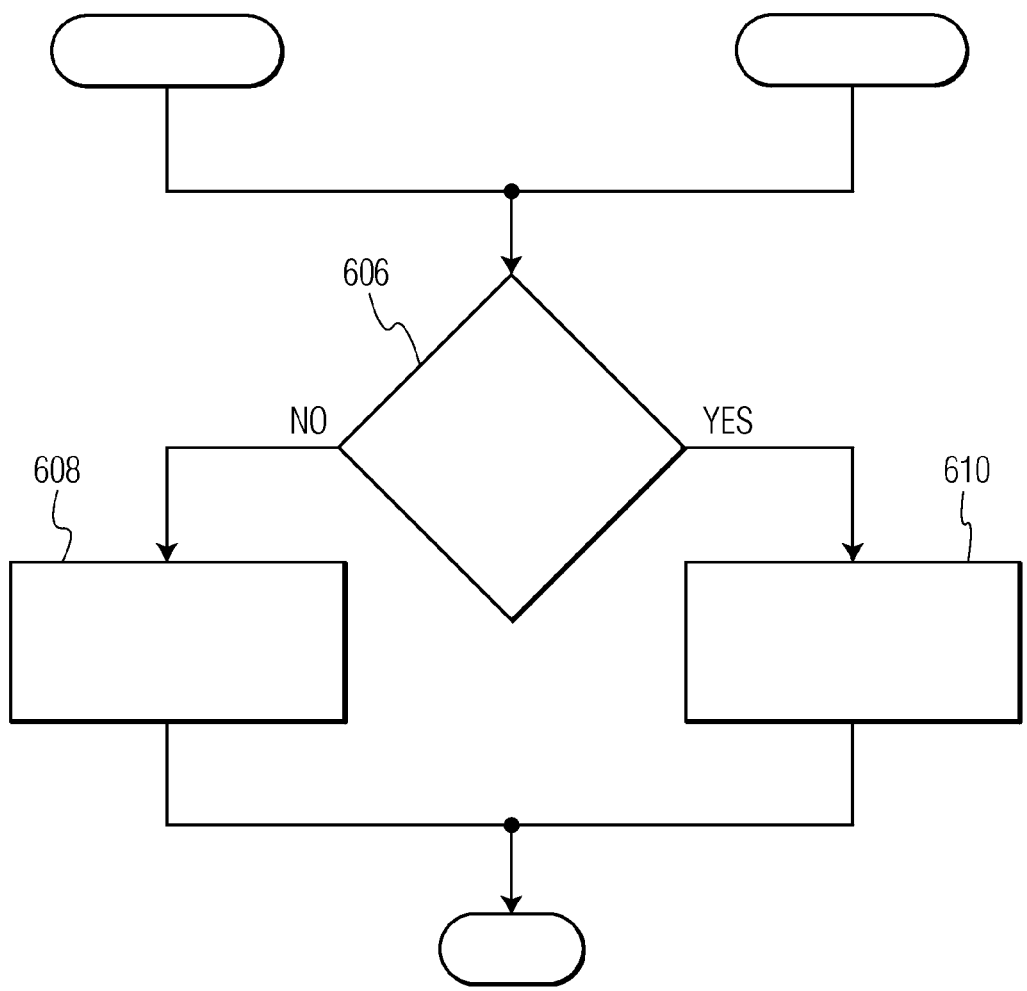
FIG. 6 is a flow diagram for enhancing the audibility of audible prompts in addition to the enhancement of FIGS. 4 and 5.

FIGS. 4-6 are flow diagrams for modifying the quality of audible prompts according to embodiments of the present invention. The processes of FIGS. 4-6 will be described with reference to the AED 110. However, modifying the quality of audible prompts according to an embodiment of the present invention can be utilized in the AED 110, OTC AED 310, as well as other defibrillators where audible prompts are used.

The quality of audible prompts can be modified so that they are tailored for a particular use and for a particular environment in which the AED 110 is used. In one embodiment, the quality of audible prompts can be manually selected or changed from a default audio quality using the user interface 214. Thus, a user can choose between various quality audible prompts and select one that is suitable for the particular situation. For example, playback of audible prompts having greater bandwidth and dynamic range (i.e., relatively good sound quality) can be selected when demonstrating the operation and various functions of the AED 110 in an environment that has relatively low ambient noise and where higher fidelity audible prompts will be appreciated. In contrast, where the AED 110 is being used during an emergency, audible prompts having decreased audio fidelity but having greater audible clarity in a noisy environment can be selected.

In another embodiment, the quality of audible prompts is automatically selected based on the mode of operation. As previously discussed, an AED can be operated in various modes, such as demonstration, administration, training, and emergency modes of operation. Each of the modes of operation can have an associated audio quality. For example, during demonstration, administration, and training modes of operation, relatively high-quality audible prompts can be used, whereas lesser-quality audible prompts tailored for increased clarity in noisy environments can be used during the emergency mode of operation.

In another embodiment, the different levels of audibility can be automatically selected based on the level of ambient noise as detected by the microphone 212. In more controlled environments with less ambient noise, the audible prompts can be played back without enhancement. However, where a noise threshold is exceeded based on the ambient noise detected by the microphone 212, the perceived clarity of the audible prompts is enhanced so that they can be heard over the noisy background. The processes of FIGS. 4-6 can be combined with the previously described techniques for determining whether the quality of the audible prompts should be modified. It will be appreciated, however, that the techniques specifically discussed are provided by way of example. Other techniques can be combined with the processes of FIGS. 4-6 as well.

FIG. 4 illustrates a process 400 for modifying the quality of audible prompts by performing signal processing on the audio data representing the audio prompts prior to playback. At step 402 an audio file for the audible prompts is retrieved from the memory 218 and provided to the audio processor 220. Examples of when the audio file is typically retrieved from memory include upon power-up of the AED 110, in response to the occurrence of an event such as changing modes of operation, anticipated use of the AED to deliver a defibrillating shock, or in response to user input through the user interface 214. The audio file is decoded by the audio processor 220 in preparation for playback of the audible prompts at step 404. At step 406 a determination is made whether the quality of the audible prompts is to be modified. In the case where audibility is not to be modified, indicating playback a default level of audibility, the audible prompts are played back at step 408 without additional processing. However, where audibility is to be modified at step 406, such as when the AED 110 is operating in a mode of operation where enhanced clarity is needed or the ambient noise as detected by the microphone 212 exceeds a threshold level, audio data of the audio file is signal processed by the DSP 222 at step 410 to modify audio quality, for example, to enhance clarity by reducing audio quality in a noisy environment.

Different signal processing now known or later developed can be utilized to improve the quality of audible prompts. One example is to take the audio data of relatively high-quality audio prompts and compress the bandwidth, and additionally or alternatively, compress the dynamic range of the audio prompts to improve audibility in a noisy environment. Another example is to low-pass filter the audio prompts to remove lower frequency content. These approaches remove frequency content that typically make the audio prompts sound of higher-quality. However, the removed frequency content is less significant when hearing and comprehending the audible prompts over loud ambient conditions is a priority. By removing some of the frequency content, the audio speaker 216 can be driven at higher volume levels without necessarily increasing distortion because, as is known, speaker drive levels and cone displacement decreases with increasing frequency. As a result, the audio system of the AED 110 can be retuned to drive a signal processed audible prompts at near full capacity to take advantage of the power bandwidth of the audio system.

FIG. 5 illustrates a process 500 for modifying the quality of audible prompts by selecting one of a plurality of audio files for playback. At step 502 a determination is made whether the quality of the audible prompts should be modified. In the case of no modification, indicating that the default audio quality is to be used, a default audio file is retrieved from the memory 218 at step 504 and decoded at step 506 for playback of the audible prompts at step 408. Where the audibility is to be modified at step 502, such as when selected by the user or the AED 110 is operating in a mode of operation where enhanced clarity is needed, an alternative audio file is retrieved from the memory 218 at step 510. The alternative audio file is decoded at step 506 for playback at step 508. The alternative audio file can be for audible prompts that have a different level of audio quality than the default audio file, such as greater compressed bandwidth and lesser dynamic range for increased clarity in a noisy environment.

In alternative embodiments of the present invention, the processes 400 and 500 can be combined with process 600 of FIG. 6 to further enhance the quality of audible prompts. The process 600 further increases audibility by using either a normal playback volume or a louder playback volume. A louder playback volume can be used without increasing distortion where the signal processing of process 400 or the alternative audio file of process 500 are tailored for reduced distortion for playback at an increased volume. Prior to actual playback of the audible prompts in processes 400 and 500, at step 606 a determination is made whether the audibility of the audible prompts is to be modified. In the case where audibility is not to be modified, the audible prompts are played back at step 608 at a first (i.e., normal) playback volume. However, where audibility is to be modified at step 606, such as when the ambient noise is greater than a threshold level, as detected by the microphone 212, the audible prompts are played back at step 610 at a second (i.e., louder) playback volume.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An automatic external defibrillator (AED), comprising:
an audio system operable to provide audible information; and
a controller coupled to the audio system and operable to control the audio system to provide the audible information and further operable to select one of a plurality of different levels of sound quality at which the audio system provides the audible information.

2. The AED of claim 1, further comprising an audio sensor operable to detect ambient noise and the controller comprises a controller operable to determine whether a detected level of ambient noise exceeds a threshold and further operable to select a first level of sound quality in response to the level of ambient noise being less than the threshold and select a second level of sound quality different than the first level in response to the level of ambient noise exceeding the threshold.

3. The AED of claim 2, further comprising a memory operable to store audio data files and an audio processor operable to process audio data files, and wherein the controller comprises a controller operable to retrieve a default audio data file representing the audible information in response to selecting the first level of sound quality and provide the same to the audio processor for playback of the audible information, and further operable to retrieve an alternative audio data file representing the audible information in response to selecting the second level of sound quality and provide the same to the audio processor for playback of the audible information.

4. The AED of claim 2, further comprising a memory operable to store audio data files, an audio processor operable to process audio data files, and a digital signal processor operable to signal process audio data files, the controller comprises a controller operable to retrieve an audio data file representing the audible information in response to selecting the first level of sound quality and provide the same to the audio processor for playback of the audible information, and further operable to provide the audio data file to the digital signal processor to be processed prior to providing the processed audio data file to the audio processor for playback.

5. The AED of claim 4 wherein the digital signal processor comprises a digital signal processor operable to signal process the audio data file by at least one of low pass filtering, compressing bandwidth, and compressing dynamic range.

6. The AED of claim 1 wherein the controller comprises a controller operable to select one of the plurality of different levels of sound quality in accordance with a mode of operation of the AED.

7. The AED of claim 6 wherein the mode of operation comprises at least one of an administrative mode, a training mode, a demonstration mode, and an emergency mode.

* * * * *